US006992105B2

(12) United States Patent
Fink

(10) Patent No.: US 6,992,105 B2
(45) Date of Patent: *Jan. 31, 2006

(54) DIPEPTIDE DERIVATIVES

(75) Inventor: Cynthia Anne Fink, Lebanon, NJ (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/884,150

(22) Filed: Jul. 2, 2004

(65) Prior Publication Data

US 2004/0235754 A1 Nov. 25, 2004

Related U.S. Application Data

(62) Division of application No. 10/142,693, filed on May 9, 2002, now Pat. No. 6,777,443.

(60) Provisional application No. 60/339,575, filed on Dec. 11, 2001, provisional application No. 60/291,088, filed on May 15, 2001.

(51) Int. Cl.
*A61K 31/325* (2006.01)
*C07C 321/00* (2006.01)

(52) U.S. Cl. ............................. 514/542; 560/9; 560/15
(58) Field of Classification Search .................. 560/9, 560/15; 514/542
See application file for complete search history.

(56) References Cited

U.S. PATENT DOCUMENTS

| | | | |
|---|---|---|---|
| 5,214,181 A | 5/1993 | Morita et al. | 558/248 |
| 5,506,244 A | 4/1996 | Fink | 514/354 |
| 5,508,266 A | 4/1996 | Fink | 514/19 |
| 5,591,891 A | 1/1997 | Fournie-Zaluski et al. | 567/426 |
| 5,801,274 A | 9/1998 | Fournie-Zaluski et al. | 562/426 |
| 5,994,293 A | 11/1999 | Baxter et al. | 514/2 |
| 6,162,828 A | 12/2000 | Fukuda et al. | 514/564 |
| 6,284,914 B1 * | 9/2001 | Fujisawa et al. | 560/13 |
| 6,492,421 B1 * | 12/2002 | Thorsett et al. | 514/562 |
| 6,495,522 B1 | 12/2002 | Wang et al. | 514/19 |
| 6,503,949 B1 | 1/2003 | Lau et al. | 514/617 |
| 6,552,079 B2 | 4/2003 | Scarborough et al. | 514/534 |
| 6,576,766 B1 * | 6/2003 | Weigele et al. | 548/414 |
| 6,635,621 B1 | 10/2003 | Singh et al. | 514/506 |
| 6,670,393 B2 | 12/2003 | Schwartz et al. | 514/506 |
| 6,803,383 B2 * | 10/2004 | Boger et al. | 514/542 |
| 2002/0004500 A1 | 1/2002 | Reeves et al. | |
| 2002/0013307 A1 | 1/2002 | Lapuerta et al. | |

FOREIGN PATENT DOCUMENTS

| | | |
|---|---|---|
| WO | WO 93/02099 | 2/1993 |
| WO | WO 99/19346 A | 4/1999 |
| WO | WO 99/24461 | 5/1999 |
| WO | WO 99/55723 | 11/1999 |
| WO | WO 99/55726 | 11/1999 |
| WO | WO 00/40600 | 7/2000 |
| WO | WO 00/43414 | 7/2000 |

OTHER PUBLICATIONS

Robl J.A. et al., "Recent Advances in the Design and Development of Vasopeptidase Inhibitors", Expert Opinion on therapeutic Patents, Ashley Publications, GB, vol. 9, No. 12, pp. 1665-1667 (1999).
Coric et al., "Optimal Recongnition of Neutral Endopeptidase and Angiotensin-Converting Enzyme Active Sites by Mercaptoacyldipeptides as a means to Design Potent Dual Inhibitors", J. Med. Chem., vol. 39, No. 6, pp. 1210-1219 (1996).
Bhagwat et al., "alpha-Mercaptoacyl Dipeptides that inhibit Angiotensin converting Enzyme and neutral Endopeptidase 24. 11", Bioorganic & Medicinal Chemistry letters, vol. 5, No. 7, pp 735-738 (1995).
Bell et al., "The Synthesis, NMR Spectroscopy, and X-ray Structure of a new Rhenium $N_2S_2$ Chelate Complex", Inorg. Chem. vol. 37, No. 14, pp. 3517-3520 (1998).

* cited by examiner

Primary Examiner—Deborah C. Lambkin
(74) Attorney, Agent, or Firm—Novartis

(57) ABSTRACT

Compounds of the formula $$R_3S-\underset{\underset{R_5}{|}}{\overset{\overset{R_4}{|}}{C}}-\overset{O}{\overset{\|}{C}}-\underset{H}{N}-\underset{\underset{R_7}{|}}{\overset{\overset{R_6}{|}}{C}}-\overset{O}{\overset{\|}{C}}-\underset{R}{N}-\underset{}{\overset{alk-X-R_1}{\underset{|}{CH}}}-COOR_2 \quad (I)$$

wherein R, $R_1$, $COOR_2$, $R_3$–$R_7$, alk, and X have meaning as defined, such being useful as dual inhibitors of angiotensin converting enzyme and neutral endopeptidase, as well as inhibitors of endothelin converting enzyme.

7 Claims, No Drawings

DIPEPTIDE DERIVATIVES

CROSS-REFERENCE TO RELATED APPLICATIONS

This is a divisional application of U.S. application Ser. No. 10/142,693 filed May 9, 2002, now U.S. Pat. No. 6,777,443 which claims the benefit of U.S. provisional application No. 60/339,575 filed on Dec. 11, 2001 and U.S. provisional application No. 60/291,088 filed on May 15, 2001, the contents of both which are incorporated herein by reference in their entirety.

SUMMARY OF THE INVENTION

The present invention directed to novel vasopeptidase inhibitors described below which are useful as dual inhibitors of both angiotensin converting enzyme (ACE) and neutral endopeptidase (NEP, EC 3.4.24.11). The compounds of the invention are particularly useful for the treatment and/or the prevention of conditions which are responsive to ACE and NEP inhibition, particularly cardiovascular disorders, such as hypertension, isolated systolic hypertension, renal failure (including edema and salt retention), pulmonary edema, left ventricular hypertrophy, heart failure (including congestive heart failure) and atherosclerosis. The compounds of the invention are also useful for reducing elevated cholesterol plasma levels in mammals. Furthermore, they also inhibit endothelin converting enzyme (ECE) and are useful for the treatment and/or prevention of conditions which are responsive to ECE inhibition.

By virtue of their inhibition of neutral endopeptidase, the compounds of the invention may also be useful for the treatment of pain, depression, certain psychotic conditions, and cognitive disorders. Other potential indications include the treatment of angina, premenstrual syndrome, Meniere's disease, hyperaldosteronism, hypercalciuria, ascites, glaucoma, asthma and gastrointestinal disorders such as diarrhea, irritable bowel syndrome and gastric hyperacidity.

By virtue of their inhibition of ECE, the compounds of the invention may also be useful for the treatment and/or prevention of endothelin dependent conditions and diseases, including cerebral ischemia (stroke), subarachnoid hemorrhage, traumatic brain injury, cerebral vasospasm, arterial hypertrophy, restenosis, Raynaud's disease, myocardial infarction, obesity; also prostate hyperplasia, migraine, diabetes mellitus (diabetic nephropathy), preeclampsia, glaucoma, and transplantation rejection such as in aorta or solid organ transplantation; as well as erectile dysfunction.

DETAILED DESCRIPTION OF THE INVENTION

The present invention relates to compounds of formula I

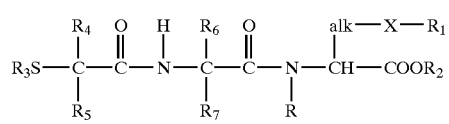

(I)

wherein

R represents hydrogen, lower alkyl, carbocyclic or heterocyclic aryl-lower alkyl or cycloalkyl-lower alkyl;

$R_1$ represents lower alkyl, cycloalkyl, carbocyclic or heterocyclic aryl, or biaryl; or $R_1$ represents (cycloalkyl, carbocyclic aryl, heterocyclic aryl or biaryl)-lower alkyl;

alk represents lower alkylene;

$R_3$ represents hydrogen or acyl;

$R_4$ represents hydrogen, optionally substituted lower alkyl, carbocyclic or heterocyclic aryl, (carbocyclic or heterocyclic aryl)-lower alkyl, cycloalkyl, cycloalkyl-lower alkyl, biaryl, biaryl-lower alkyl, oxacycloalkyl, thiacycloalkyl, azacycloalkyl, or (oxacycloalkyl, thiacycloalkyl or azacycloalkyl)-lower alkyl;

$R_5$ represents hydrogen or lower alkyl; or $R_4$ and $R_5$, together with the carbon atom to which they are attached, represent cycloalkylidene, benzo-fused cycloalkylidene; or 5- or 6-membered (oxacycloalkylidene, thiacycloalkylidene or azacycloalkylidene), each optionally substituted by lower alkyl or aryl-lower alkyl;

$R_6$ represents lower alkyl, carbocyclic or heterocyclic aryl, (carbocyclic or heterocyclic aryl)-lower alkyl, cycloalkyl, cycloalkyl-lower alkyl, biaryl or biaryl-lower alkyl;

$R_7$ represents lower alkyl, (carbocyclic or heterocyclic aryl)-lower alkyl, cycloalkyl-lower alkyl or biaryl-lower alkyl; or $R_6$ and $R_7$, together with the carbon atom to which they are attached, represent 3- to 10-membered cycloalkylidene which may be substituted by lower alkyl or aryl-lower alkyl or may be fused to a saturated or unsaturated carbocyclic 5- to 7-membered ring; or 5- or 6-membered (oxacycloalkylidene, thiacycloalkylidene or azacycloalkylidene), each optionally substituted by lower alkyl or aryl-lower alkyl; or 2,2-norbonylidene;

X represents —O—, —S(O)$_n$—, —NHCO$_2$—, or —NHCO—;

n is zero, one or two; and

COOR$_2$ represents carboxyl or carboxyl derivatized in form of a pharmaceutically acceptable ester;

disulfide derivatives derived from said compounds wherein $R_3$ is hydrogen; and pharmaceutically acceptable salts thereof.

The present invention is also directed to pharmaceutical compositions comprising said compounds; methods for preparation of said compounds; intermediates; and methods of treating disorders in mammals which are responsive to ACE and NEP inhibition by administration of said compounds to mammals in need of such treatment.

Encompassed by the instant invention are also any prodrug derivatives of compounds of the invention having a free carboxyl, sulfhydryl or hydroxy group, said prodrug derivatives being convertible by solvolysis or under physiological conditions to be the free carboxyl, sulfhydryl and/or hydroxy compounds. Prodrug derivatives are, e.g., the esters of free carboxylic acids and S-acyl and O-acyl derivatives of thiols, alcohols or phenols, wherein acyl has meaning as defined herein.

Pharmaceutically acceptable esters are preferably prodrug ester derivatives, such being convertible by solvolysis or under physiological conditions to the free carboxylic acids of formula I.

Pharmaceutically acceptable prodrug esters are preferably, e.g., lower alkyl esters, aryl-lower alkyl esters, α-(lower alkanoyloxy)-lower alkyl esters such as the pivaloyloxymethyl ester, and α-(lower alkoxycarbonyl, morpholinocarbonyl, piperidinocarbonyl, pyrrolidinocarbonyl or di-lower alkylaminocarbonyl)-lower alkyl esters.

Pharmaceutically acceptable salts are salts derived from pharmaceutically acceptable bases for any acidic compounds of the invention, e.g., those wherein COOR$_2$ represents carboxyl. Such are, e.g., alkali metal salts (e.g., sodium, potassium salts), alkaline earth metal salts (e.g., magnesium, calcium salts), amine salts (e.g., tromethamine salts).

Compounds of formula I, depending on the nature of substituents, possess two or more asymmetric carbon atoms. The resulting diastereomers and optical antipodes are encompassed by the instant invention. The preferred configuration is indicated in formula Ia.

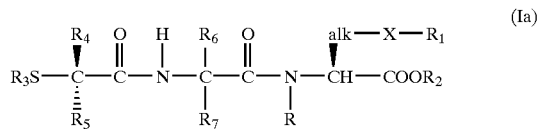

wherein asymmetric carbons carrying the substituents -alk-X—R$_1$ and R$_4$ typically have the S-configuration.

Preferred are the compounds of formula I and la wherein R and R$_5$ represent hydrogen; R$_1$ represents lower alkyl, C$_5$- or C$_6$-cycloalkyl, carbocyclic or heterocyclic aryl, or (carbocyclic or heterocyclic aryl)-lower alkyl; alk represents lower alkylene; X represents —O— or —S(O)$_n$ wherein n represents zero or two; R$_3$ represents hydrogen or acyl; R$_4$ represents optionally substituted lower alkyl, oxacycloalkyl, oxacycloalkyl-lower alkyl, or (carbocyclic or heterocyclic aryl)-lower alkyl; R$_5$ represents hydrogen; or R$_4$ and R$_5$ combined with the carbon atom to which they are attached represent C$_5$ or C$_6$-cycloalkylidene; R$_6$ and R$_7$ represent lower alkyl; or R$_6$ and R$_7$, together with the carbon atom to which they are attached, represent 5- or 6-membered cycloalkylidene; COOR$_2$ represents carboxyl or carboxyl derivatized in form of a pharmaceutically acceptable ester; disulfide derivatives derived from said compounds wherein R$_3$ is hydrogen; and pharmaceutically acceptable salts thereof.

Further preferred are said compounds of formula I and Ia wherein R and R$_5$ represent hydrogen; R$_1$ represents carbocyclic or heterocyclic aryl or (carbocyclic or heterocyclic aryl)-lower alkyl; R$_3$ represents hydrogen or optionally substituted lower alkanoyl; R$_4$ represents lower alkyl, cycloalkyl, tetrahydropyranyl or C$_1$–C$_4$-lower alkoxy-lower alkyl; R$_6$ and R$_7$ both represent C$_1$–C$_4$-alkyl and are identical; X represents —O— or —S—; alk represents methylene; COOR$_2$ represents carboxyl, lower alkoxycarbonyl, (di-lower alkylaminocarbonyl)-lower alkoxycarbonyl or (morpholinocarbonyl, piperidinocarbonyl or pyrrolidinocarbonyl)-lower alkoxycarbonyl; and pharmaceutically acceptable salts thereof.

Particularly preferred are said compounds of formula I or Ia wherein R and R$_5$ represent hydrogen; R$_1$ represents carbocyclic aryl or carbocyclic aryl-lower alkyl in which carbocyclic aryl represents phenyl or phenyl substituted by one or two of hydroxy, lower alkanoyloxy, lower alkyl, lower alkoxy, trifluoromethyl, trifluoromethoxy or halo; R$_3$ represents hydrogen, lower alkanoyl or lower alkanoyl substituted by lower alkoxy; R$_4$ represents lower alkyl, 4-tetrahydropyranyl or C$_1$–C$_4$-lower alkoxy-C$_1$–C$_4$-lower alkyl; R$_6$ and R$_7$ represent methyl; X represents —O—; alk represents methylene or ethylene; and COOR$_2$ represents carboxyl or lower alkoxycarbonyl; and pharmaceutically acceptable salts thereof. An embodiment thereof relates to compounds wherein R$_3$ represents hydrogen or lower alkanoyl.

Further preferred are the above compounds of formula I or Ia wherein R and R$_5$ represent hydrogen; R$_1$ represents phenyl, fluorophenyl, benzyl or fluorobenzyl; R$_3$ represents hydrogen, lower alkanoyl or lower alkanoyl substituted by lower alkoxy; R$_4$ represents isopropyl, tert-butyl, 1-methoxyethyl or 4-tetrahydropyranyl; R$_6$ and R$_7$ represent methyl; X represents —O—; alk represents methylene; and COOR$_2$ represents carboxyl or lower alkoxycarbonyl; and pharmaceutically acceptable salts thereof. An embodiment thereof relates to compounds wherein R$_3$ represents hydrogen or lower alkanoyl.

Preferred particular embodiments relate to compounds of formula I or Ia wherein R and R$_5$ represent hydrogen; R$_1$ represents benzyl; R$_3$ represents hydrogen, acetyl or methoxyacetyl; R$_4$ represents isopropyl or tert-butyl; R$_6$ and R$_7$ represent methyl; X represents —O—; alk represents methylene; and COOR$_2$ represents carboxyl or ethoxycarbonyl; or a pharmaceutically acceptable salt thereof.

The definitions as such or in combination as used herein, unless denoted otherwise, have the following meanings within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substituents, such being advantageously lower alkyl, hydroxy, lower alkoxy, acyloxy, halogen, cyano, trifluoromethyl, trifluoromethoxy, amino, lower alkanoylamino, lower alkyl-(thio, sufinyl or sulfonyl), lower alkoxycarbonyl, mono- or di-lower alkylcarbamoyl, or mono- or di-lower alkylamino; or phenyl substituted by lower alkylenedioxy.

Bicyclic carbocyclic aryl represents 1- or 2-naphthyl or 1- or 2-naphthyl preferably substituted by lower alkyl, lower alkoxy or halogen.

Monocyclic heterocyclic aryl represents preferably optionally substituted thiazolyl, pyrimidyl, triazolyl, thienyl, furanyl or pyridyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Optionally substituted pyrimidyl represents, e.g., 2-pyrimidyl or 2-pyrimidyl substituted by lower alkyl.

Optionally substituted thiazolyl represents, e.g., -2-thiazolyl or 2-thiazolyl substituted by lower alkyl.

Optionally substituted triazolyl represents, e.g., 1,2,4-triazolyl or 1,2,4-triazolyl preferably substituted by lower alkyl.

Bicyclic heterocyclic aryl represents preferably indolyl, benzothiazolyl, quinolinyl or isoquinolinyl optionally substituted by hydroxy, lower alkyl, lower alkoxy or halogen, advantageously 3-indolyl, 2-benzothiazolyl or 2- or 4-quinolinyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl; also, optionally substituted naphthyl.

Aryl-lower alkyl is advantageously benzyl or 1- or 2-phenethyl optionally substituted on phenyl by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up and including 4 and advantageously one or two carbon atoms. Such may be straight chain or branched.

Optionally substituted lower alkyl refers to lower alkyl or lower alkyl substituted by, e.g., halo, hydroxy, lower alkoxy, amino, (mono- or di-lower alkyl) amino, acylamino, 1-lower alkyl-piperazino, morpholino, piperidino, pyrrolidino and the like.

Lower alkylene refers to a straight or branched carbon chain having preferably 1 to 4 carbon atoms, which may be substituted, e.g., by lower alkoxy, for example, —CH$_2$—, —CH(CH$_3$)—, —CH$_2$CH$_2$— and the like.

A lower alkyl group preferably contains 1–4 carbon atoms which may be straight chain or branched and represents, for example, ethyl, propyl, butyl or advantageously methyl.

A lower alkoxy group preferably contains 1–4 carbon atoms which may be straight chain or branched and represents, for example, methoxy, propoxy, isopropoxy or advantageously ethoxy.

Cycloalkyl represents a saturated cyclic hydrocarbon radical which preferably contains 5- to 7-ring carbons, preferably cyclopentyl or cyclohexyl.

Oxacycloalkyl represents preferably 5- to 7-membered oxacycloalkyl, e.g., tetrahydropyranyl, such as 4-tetrahydropyranyl.

Thiacycloalkyl represents preferably 5- to 7-membered thiacycloalkyl, e.g., tetrahydrothiopyranyl, such as 4-tetrahydrothiopyranyl.

Azacycloalkyl represents preferably 5- to 7-membered azacycloalkyl, e.g., pyrrolidinyl or piperidinyl in which the nitrogen may be substituted by lower alkyl or aryl-lower alkyl.

The term cycloalkyl-lower alkyl represents preferably (cyclopentyl or cyclohexyl)-methyl, 1- or 2-(cyclopentyl or cyclohexyl)ethyl, 1-, 2- or 3-(cyclopentyl or cyclohexyl) propyl, or 1-, 2-, 3- or 4-(cyclopentyl or cyclohexyl)-butyl. Similarly (oxacyclyl, thiacycloalkyl or azacycloalkyl)-lower alkyl.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Cycloalkylidene is 3- to 10-membered, preferably 5- or 6-membered, and represents a cycloalkane linking group in which the two attached groups are attached to the same carbon of the cycloalkane ring.

5- or 6-membered oxacycloalkylidene represents a tetrahydrofuran or tetrahydropyran linking group, i.e., tetrahydrofuranylidene or tetrahydropyranylidene, in which the two attached groups are attached to the same carbon atom of the respective rings, e.g., at the 3- or 4-position thereof.

5- or 6-membered thiacycloalkylidene represents a tetrahydrothiophene or tetrahydrothiopyran linking group in which the two attached groups are attached to the same carbon atom of the respective rings, e.g., at the 3- or 4-position thereof.

5- or 6-membered azacycloalkylidene represents a pyrrolidine or piperidine linking group in which the two attached groups are attached to the same carbon atom of the respective rings, e.g., at the 3- or 4-position thereof, and the nitrogen may be substituted by lower alkyl, e.g., methyl, or by aryl-lower alkyl, e.g., benzyl.

Benzo-fused cycloalkylidene represents, e.g., 1,1- or 2,2-tetralinylidene or 1,1- or 2,2-indanylidene.

Halogen (halo) preferably represents fluoro or chloro, but may also be bromo or iodo.

Acyl is derived from a carboxylic acid and represents preferably optionally substituted lower alkanoyl, carbocyclic aryl-lower alkanoyl, aroyl, lower alkoxycarbonyl or aryl-lower alkoxycarbonyl, advantageously optionally substituted lower alkanoyl, or aroyl.

Lower alkanoyl is preferably acetyl, propionyl, butyryl, or pivaloyl.

Optionally substituted lower alkanoyl, for example, represents lower alkanoyl or lower alkanoyl substituted by, e.g., lower alkoxycarbonyl, lower alkanoyloxy, lower alkanoylthio, lower alkoxy, lower alkylthio, hydroxy, di-lower alkylamino, lower alkanoylamino, morpholino, piperidino, pyrrolidino, 1-lower alkylpiperazino, aryl or heteroaryl.

Aroyl is carbocyclic or heterocyclic aroyl, preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Acyloxy is preferably optionally substituted lower alkanoyloxy, lower alkoxycarbonyloxy, monocyclic carbocyclic aroyloxy or monocyclic heterocyclic aroyloxy.

Aryl-lower alkoxycarbonyl is preferably monocyclic carbocyclic-lower alkoxycarbonyl, advantageously benzyloxycarbonyl.

Biaryl represents monocarbocyclic aryl substituted by monocyclic carbocyclic or monocyclic heterocyclic aryl, and preferably represents biphenylyl, advantageous 4-biphenylyl optionally substituted on one or both benzene rings by lower alkyl, lower alkoxy, halogen or trifluoromethyl.

Biaryl-lower alkyl is preferably 4-biphenylyl-lower alkyl, advantageously 4-biphenylyl-methyl.

The novel compounds of the invention are ACE inhibitors inhibiting the conversion of angiotensin I to the pressor substance angiotensin II and thus decrease blood pressure in mammals. Furthermore, compounds of the invention demonstrate inhibition of NEP and thus potentiate the cardiovascular (e.g., diuretic and natriuretic) effects of atrial natriuretic factors (ANF). The combined effect is beneficial for the treatment of cardiovascular disorders in mammals, in particular, hypertension, cardiac conditions such as congestive heart failure, and renal failure. A further beneficial effect of the compounds of the invention in the treatment of said cardiovascular disorders is the inhibition of ECE.

The above-cited properties are demonstrable in vitro and in vivo tests, using advantageously mammals, e.g., mice, rats, dogs, monkeys, or isolated organs, tissues and preparations thereof. Said compounds can be applied in vitro in the form of solutions, e.g., preferably aqueous solutions, and in vivo either enterally, parenterally, advantageously, orally (p.o.) or intravenously (i.v.), e.g., as a suspension or in aqueous solution. The dosage in vitro may range between about $10^{-6}$ molar and $10^{-9}$ molar concentrations. The dosage in vivo may range, depending on the route of administration, between about 0.01 and 50 mg/kg, advantageously between about 0.1 and 25 mg/kg.

In vitro testing is most appropriate for the free carboxylic acids of the invention. The test compound is dissolved in dimethyl sulfoxide, ethanol or 0.25 M sodium bicarbonate solution, and the solution is diluted with buffer to the desired concentration.

The in vitro inhibition of the ACE by the compounds of this invention can be demonstrated by a method analogous to that given in Biochem. Pharmacol., Vol. 20, p.1637 (1971). The buffer for the ACE assay is 300 mM NaCl, 100 mM $KH_2PO_4$ (pH 8.3). The reaction is initiated by the addition of 100 μL of hippuryl-histidyl-leucine (2 mg/mL) to tubes containing enzyme and drug in a volume of 150 μL and tubes are incubated for 30 minutes at 37° C. The reaction is terminated by the addition of 0.75 mL 0.6 N NaOH. 100 μL of freshly prepared O-pthaldehyde solution (2 mg/mL in methanol) is added to the tubes, the contents are mixed and allowed to stand at room temperature. After 10 minutes, 100 μL of 6 N HCl is added. The tubes are centrifuged and the supernatant optical density is read at 360 nM. The results are plotted against drug concentration to determine the $IC_{50}$, i.e., the drug concentration which gives half the activity of the control sample containing no drug.

Typically, the compounds of invention demonstrate an $IC_{50}$ in the range of about 0.1–50 nM for ACE inhibition.

Illustrative of the invention, the compound of Example 6(a) demonstrates an $IC_{50}$ of about 20 nM in the ACE in vitro assay.

Inhibition of ACE can be demonstrated in vivo on p.o. or i.v. administration by measuring inhibition of the angiotensin I induced pressor response in normotensive rats.

The in vivo test for i.v. administered compounds is performed with male, normotensive rats, which are conscious. A femoral artery and femoral vein are cannulated respectively for direct blood pressure measurement on i.v. administration of angiotensin I and i.v. or p.o. administration of a compound of this invention. After the basal blood pressure is stabilized, pressor responses to 3 or 4 challenges of 300 ng/kg angiotensin I i.v., at 15-minute intervals, are obtained. Such pressure responses are usually again obtained at 15, 30, 60 and 90 minutes, and then every hour up to 6 hours after i.v. or p.o. administration of the compound to be tested, and compared with the initial responses. Any observed decrease of said pressor response is an indication of ACE inhibition.

Illustrative of the invention, the compound of Example 6(a) inhibits the angiotensin I induced pressor response for 3 hours at a dose of 10 mg/kg i.v. Similarly, the compound of Example 1(a) inhibits the angiotensin I induced pressor response for 6 hours at a dose of 11.8 mg/kg p.o.

The in vitro inhibition of NEP (EC 3.4.24.11) can be determined as follows:

NEP 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 μL) contains 4.2 μL of protein (rat kidney cortex membranes prepared by method of Maeda et al., 1983), 50 mM tris buffer, pH 7.4 at 25° C., 500 μM substrate (final concentration), and leucine aminopeptidase M (2.5 μg). The mixture is incubated for 10 minutes at 25° C., and 100 μL of fast garnet (250 μg fast garnet/mL of 10% Tween 20 in 1 M sodium acetate pH 4.2) is added. Enzyme activity is measure spectrophotometrically at 540 nM. One unit of NEP 24.11 activity is defined as 1 nmol of 2-naphthylamine released per minute at 25° C. at pH 7.4. $IC_{50}$ values are determined, i.e., the concentration of test compound required for 50% inhibition of the release of 2-naphthylamine.

NEP activity can also be determined using ANF as a substrate. ANF degrading activity is determined by measuring the disappearance of rat-ANF (r-ANF) using a 3-minute reverse phase-HPLC separation. An aliquot of the enzyme in 50 mM tris HCl buffer, pH 7.4, is pre-incubated at 37° C. for 2 minutes and the reaction is initiated by the addition of 4 nmol of r-ANF in a total volume of 50 μL. The reaction is terminated after 4 minutes with the addition of 30 μL of 0.27% trifluoroacetic acid (TFA). One unit of activity is defined as the hydrolysis of 1 nmol of r-ANF per minute at 37° C. at pH 7.4. $IC_{50}$ values are determined, i.e., the concentration of test compound required for 50% inhibition of the hydrolysis of ANF.

Typically, the compounds of the invention demonstrate an $IC_{50}$ in the range of about 0.1–50 nM for NEP inhibition.

Illustrative of the invention, the compound of Example 6(a) demonstrates an $IC_{50}$ of about 5 nM in the GAAP in vitro assay.

The effect of the compounds of the invention on rat plasma ANF concentration can be determined as follows:

Male Sprague-Dawley rats (275–390 g) are anesthetized with ketamine (150 mg/kg)/acepromazine (10%) and instrumented with catheters in the femoral artery and vein to obtain blood samples and infuse ANF, respectively. The rats are tethered with a swivel system and are allowed to recover for 24 hours before being studied in the conscious, unrestrained state.

In the assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180 and 240 minutes after administration of the test compound.

Plasma ANF concentrations are determined by a specific radioimmunoassay. The plasma is diluted (×12.5, ×25 and ×50) in buffer containing: 50 mM tris (pH 6.8), 154 mM NaCl, 0.3% bovine serum albumin, 0.01% EDTA. One hundred microliters of standards [rANF (99–126)] or samples are added to 100 μL of rabbit anti-rANF serum and incubated at 4° C. for 16 hours. Ten thousand cpm of [$^{125}$I]rANF are then added to the reaction mixture which is incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supernatant is decanted and the pellets counted in a gamma counter. All determinations are performed in duplicate. Plasma ANF levels are expressed as a percent of those measured in vehicle-treated animals which received ANF alone (450 ng/kg/min. i.v.)

Illustrative of the invention, the compound of Example 1(a) increases plasma ANF levels by about 70% at a dose of 11.8 mg/kg p.o.

The anti-hypertensive activity can be determined, e.g., in the spontaneously hypertensive rat (SHR) and the DOCA-salt hypertensive rat, e.g., according to Bazil et al., J. Cardiovasc. Pharmacol., Vol. 22, pp. 897–905 (1993) and Trapani et al., J. Cardiovasc. Pharmacol., Vol. 14, pp. 419–424 (1989), respectively.

Illustrative of the invention, the compound of example 1(a) reduces mean arterial pressure in conscious SHR at once daily administration of 11.8 mg/kg p.o.

The anti-hypertensive effect can be determined in desoxycorticosterone acetate (DOCA)-salt hypertensive rats as follows:

DOCA-salt hypertensive rats (280–380 g) are prepared by the standard method. Rats undergo a unilateral nephrectomy and one week later are implanted with silastic pellets containing 100 mg/kg of DOCA. The rats are maintained on 1% of NaCl/0.2% KCl drinking water for three to five weeks until sustained hypertension is established. The anti-hypertensive activity is evaluated at this time.

Two days before an experiment, the rats are anesthetized with methoxyflurane and instrumented with catheters in the femoral artery to measure arterial blood pressure. Forty-eight hours later, baseline arterial pressure and heart rate are recorded during a one hour period. The test compound or vehicle is then administered and the same cardiovascular parameters are monitored for an additional 5 hours.

The diuretic (saluretic) activity can be determined in standard diuretic screens, e.g., as described in "New Anti-hypertensive Drugs", Spectrum Publications, pp. 307–321 (1976), or by measuring the potentiation of ANF-induced natriuresis and diuresis in the rat.

The potentiation of the natriuretic effect of ANF can determined as follows:

Male Sprague-Dawley rats (280–360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 µL/min.) is maintained throughout the experiment to promote diuresis and sodium excretion. The experimental protocol consists of an initial 15-minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control, 15 minutes). At the conclusion of this period, ANF is administered (1 µg/kg i.v. bolus) to all animals and arterial pressure and renal parameters are determined during two consecutive 15-minute collection periods. Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

The in vitro inhibition of ECE can be determined as follows:

ECE is partially purified from porcine primary aortic endothelial cells by DE52 anion exchange column chromatography and its activity is quantified by radioimmunoassay (RIA) as described in Anal. Biochem., Vol., 212, pp. 434–436 (1993). Alternatively, the native enzyme can be substituted by a recombinant form of ECE, as described, for example, in Cell, Vol. 78, pp. 473–485 (1994). Human ECE-1 has been described by several groups (Schmidt et al., FEBS Letters, Vol. 356, pp. 238–243 (1994); Kaw et al., 4th Int. Conf. on Endothelin; April 23–25, London (UK) (1995) C6; Valdenaire et al., J. Biol. Chem., Vol. 270, pp. 29794–29798 (1995); Shimada et al., Biochem. Biophys. Res. Commun., Vol. 207, pp. 807–812 (1995)). The ECE inhibition can be determined as described in Biochem. Mol. Biol. Int., Vol. 31, No. 5, pp. 861–867 (1993), by RIA to measure ET-1 formed from big ET-1.

Alternatively, recombinant human ECE-1 (rhECE-1) can be used, as follows:

Chinese hamster ovary cells expressing rhECE-1 (Kaw et al., 4th Int. Conf. on Endothelin; April 23–25, London (UK) (1995) C6) are cultured in DMEM/F12 medium containing 10% fetal bovine serum and 1× antibiotic-antimycotic. Cells are harvested by scraping, pelleted by centrifugation, and homogenized at 4° C. in a buffer containing 5 mM $MgCl_2$, 1 µM pepstatin A, 100 µM leupeptin, 1 mM PMSF, and 20 mM Tris, pH 7.0, with a ratio of 2 mL of buffer/mL of cells. The cell debris is removed by brief centrifugation, and the supernatant is centrifuged again at 100,000×g for 30 minutes. The resulting pellet is re-suspended in a buffer containing 200 mM NaCl and 50 mM Tes, pH 7.0, at a protein concentration about 15 mg/mL and stored in aliquots at −80° C.

To assess the effect of an inhibitor on ECE-1 activity, 10 µg of protein is pre-incubated with the compound at a desired concentration for 20 minutes at room temperature in 50 mM TES, pH 7.0, and 0.005% Triton X-100 in a volume of 10 µL. Human big ET-1 (5 µL) is then added to a final concentration of 0.2 µM, and the reaction mixture is further incubated for 2 hours at 37° C. The reaction is stopped by adding 500 µL of RIA buffer containing 0.1% Triton X-100, 0.2% bovine serum albumin, and 0.02% $NaN_3$ in phosphate-buffered saline.

Diluted samples (200 µL) obtained from the above enzyme assay are incubated at 4° C. overnight with 25 µL each of $[^{125}I]ET-1$ (10,000 cpm/tube) and 1:20,000-fold diluted rabbit antibodies that recognize specifically the carboxyl terminal tryptophan of ET-1. Goat anti-rabbit antibodies coupled to magnetic beads (70 µg) are then added to each tube, and the reaction mixture is further incubated for 30 minutes at room temperature. The beads are pelleted using a magnetic rack. The supernatant is decanted, and the radioactivity in the pellet is counted in a gamma counter. Total and nonspecific binding are measured in the absence of non-radioactive ET-1 and anti-ET antibodies, respectively. Under these conditions, ET-1 and big ET-1 displace $[^{125}I]$ ET-1 binding to the antibodies with $IC_{50}$ values of 21±2 and 260,000±66,000 fmol (mean±SEM, n=3–5), respectively.

In order to determine the $IC_{50}$ value of an inhibitor, a concentration-response curve of each inhibitor is determined. An IBM-compatible version of ALLFIT program is used to fit data to a one-site model.

ECE inhibition can also be determined in vivo by measuring the inhibition of big ET-1-induced pressor response in the anesthesized or conscious rat, as described below. The effect of the inhibitors on the pressor response resulting from big ET-1 challenge is measured in Sprague-Dawley rats as described in Biochem. Mol. Biol. Int., Vol. 31, No. 5, pp. 861–867 (1993). Results are expressed as percent inhibition of the big ET-1-induced pressor response as compared to vehicle.

Male Sprague-Dawley rats are anesthetized with Inactin (100 mg/kg i.p.) and instrumented with catheters in the femoral artery and vein to record mean arterial pressure (MAP) and administer compounds, respectively. A tracheostomy is performed and a cannula inserted into the trachea to ensure airway patency. The body temperature of the animals is maintained at 37±1° C. by means of a heating blanket. Following surgery, MAP is allowed to stabilize before interrupting autonomic neurotransmission with chlorisondamine (3 mg/kg i.v.). Rats are then treated with the test compound at 10 mg/kg i.v. or vehicle and challenged with big ET-1 (1 nmol/kg i.v.) 15 and 90 minutes later. Generally, the data are reported as the maximum increase in MAP produced by big ET-1 in animals treated with the test compound or vehicle.

Male Sprague-Dawley rats are anesthetized with methohexital sodium (75 mg/kg i.p.) and instrumented with catheters in the femoral artery and vein to measure MAP and administer drugs, respectively. The catheters are threaded through a swivel system that enables the rats to move freely after regaining consciousness. The rats are allowed to recover from this procedure for 24 hours before initiating the study. On the following day, MAP is recorded via the femoral artery catheter and a test compound or vehicle is administered via the femoral vein. Animals are challenged with big ET-1 at 1 nmol/kg i.v. at various times after dosing. After an adequate washout period, depending upon the dose and regimen, animals can be re-tested at another dose of test compound or vehicle. Generally, the data are reported as the change in MAP produced by big ET-1 at 2-minute intervals in animals treated with the test compound as compared to vehicle.

ECE inhibition can also be determined in vivo by measuring the inhibition of the big ET-1 induced pressor response in conscious SHR, e.g. as described in Biochem. Biophys. Res. Commun., Vol. 204, pp. 407–412 (1994).

Male SHR (16–18 weeks of age) are administered either test compound or vehicle (1 M NaHCO$_3$) via an osmotic minipump implanted subcutaneously. On day 5, femoral arterial and venous catheters are placed in anesthetized rats for the measurement of MAP and for test compound administration, respectively. After a 48-hour recovery period, MAP is recorded (day 7) through the arterial catheter connected to a pressure transducer. Blood pressure and heart rate are allowed to stabilize for 30 minutes before ganglion blockade is performed using chlorisondamine (10 mg/kg i.v.). Approximately 15 minutes later, a bolus dose of big ET-1 (0.25 nmol/kg i.v.) is administered to both vehicle- and test compound-treated rats. The change in blood pressure in response to big ET-1 is then compared between the two groups of rats.

The inhibition of cerebral vasospasm is demonstrated by measuring the inhibition of experimentally induced constriction of basilar cerebral arteries in the rabbit (Caner et al., J. Neurosurg., Vol. 85, pp. 917–922 (1996).

The degree or lack of undesirable immunostimulatory potential of the compounds of the invention can be determined with the murine popliteal lymph node assay described in Toxicology Letters, Vols. 112/113, pp. 453–459 (2000).

The compounds of the invention, e.g., can be prepared a) by condensing a compound of formula II

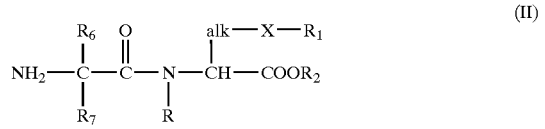

wherein the symbols alk, X, R, $R_1$, $R_6$ and $R_7$ have the meaning as defined above and COOR$_2$ represents esterified carboxyl, with a carboxylic acid of the formula III

or a reactive functional derivative thereof, wherein $R_4$ and $R_5$ have meaning as defined above; $R_3$' represents hydrogen or a labile S-protecting group, e.g., acyl, t-butyl or optionally substituted benzyl; or b) by condensing a compound of the formula IV

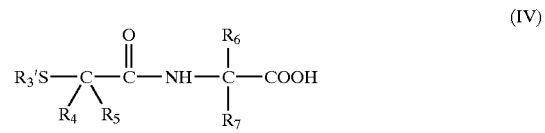

or a reactive functional derivative thereof wherein the symbols $R_3$', $R_4$–$R_5$ and $R_6$–$R_7$ have meaning as defined above, with an amino acid ester of the formula V

wherein alk, X, R and $R_1$ have meaning as defined above and COOR$_2$ represents esterified carboxyl; or c) by condensing under basic conditions a compound of the formula VI

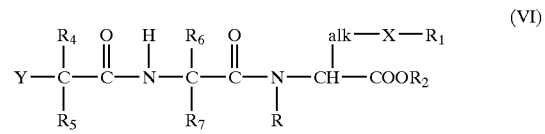

wherein the symbols R, $R_1$, COOR$_2$, $R_4$–$R_7$, alk and X have meaning as defined above and Y represents a reactive esterified hydroxyl group (e.g., chloro or bromo) as a leaving group, with a compound of the formula

or a salt thereof, wherein $R_3$' represents a labile S-protecting group, e.g., acyl, t-butyl or optionally substituted benzyl; and converting a resulting product to a compound of formula I wherein $R_3$ is hydrogen;

and in above said process, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates, and/or, if desired, resolving a racemate obtained into the optical antipodes.

In starting compounds and intermediates which are convened to the compounds of the invention in manner described herein, functional group present, such as thiol, carboxyl, amino and hydroxy groups, are optionally protected by conventional protecting groups that are common in preparative organic chemistry. Protected thiol, carboxyl, amino and hydroxy groups are those that can be converted under mild conditions into free thiol, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (thiol, carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. (1973), T. W. Greene and P. G. M. Wuts, "Protective Groups in Organic Synthesis", Wiley, N.Y. 3$^{rd}$ Ed. (1999), and also in "The Peptides", Vol. I, Schroeder and Luebke, Academic Press, London, N.Y. (1965).

The preparation of compounds of the invention according to process (a) involving the condensation of an amine of formula II with the acid of formula III or a functional reactive derivative thereof, is carried out by methodology well-known for peptide synthesis.

The condensation according to process (a) of an amino ester of formula II with a free carboxylic acid of formula III is carried out advantageously in the presence of a condensing agent such as dicyclohexylcarbodiimide, N-(3-dimethylaminopropyl)-N'-ethylcarbodiimide, hydroxybenzotriazole, 1-hydroxy-7-azabenzotriazole, chlorodimethoxytriazine, benzotriazol-1-yloxytris(dimethylamino)phosphonium hexafluorophosphate (BOP Reagent), or O-(7-azabenzotriazol-1-yl)-N,N,N',N'-tetramethyluronium hexafluorophosphate (HATU), either alone or in combination, and triethylamine or N-methylmorpholine, in an inert polar solvent, such as ethyl acetate, acetonitrile, dimethylformamide or methylene chloride, preferably at room temperature.

The condensation of an amino ester of formula II with a reactive functional derivative of an acid of formula III in the form of an acid halide, advantageously an acid chloride, or mixed anhydride, is carried out in an inert solvent such as toluene or methylene chloride, advantageously in the presence of a base, e.g., an inorganic base such as potassium carbonate or an organic base such as triethylamine, N-methylmorpholine or pyridine, preferably at room temperature.

Reactive functional derivatives of carboxylic acids of formula III are preferably acid halides (e.g., the acid chloride) and mixed anhydrides, such as the pivaloyl or isobutyloxycarbonyl anhydride, or activated esters such as benzotriazole, 7-azabenzotriazole or hexafluorophenyl ester.

The starting material of formula II can be prepared according to methods described herein and illustrated in the examples.

The preparation of a starting material of formula II involves the acylation of an ester of formula VIII

(VIII)

wherein alk, X, R and $R_1$ have meaning as defined hereinabove and COOR$_2$ represents esterified carboxyl (e.g., wherein $R_2$ is lower alkyl or benzyl) with an appropriately N-protected amino acid (or a reactive functional derivative) of formula IX

(IX)

wherein $R_6$ and $R_7$ have meaning as defined hereinabove and $R_8$ is a labile amino protecting group, e.g., t-butoxycarbonyl, to obtain the corresponding N-protected compound of formula II.

The condensation of a compound of formula VIII with a compound of formula IX is carried out by methodology well-known in peptide synthesis, e.g., as described above for the condensation of a compound of formula II with a compound of formula III. The N-protecting group is removed according to methods well-known in the art, e.g., the t-butoxycarbonyl is removed with anhydrous acid such as trifluoroacetic acid or HCl.

The starting amino esters and acids of compounds of formula VIII and IX, respectively, are either known in the art, or if new, can be prepared according to methods well-known in the art, e.g., or illustrated herein. The amino acid esters of formula VIII are preferably the S-enantiomers.

The starting materials of formula III are known, or if new, may be prepared according to conventional methods. The starting materials are prepared, e.g., from the corresponding racemic or optically active α-amino acids, by conversion thereof to the α-bromo derivative followed by displacement thereof with inversion of configuration using the appropriate thiol derivative of formula VII, under basic conditions, for example, as illustrated in European Patent Application No. 524,553 published Jan. 27, 1993. S-debenzylation of the resulting final products is carried out by reductive cleavage, e.g., with Raney nickel in ethanol. S-deacylation is carried out by, e.g., base catalyzed hydrolysis with dilute aqueous sodium hydroxide. Cyclic starting materials of formula III can be prepared by treatment of the cyclic carboxylic acid (e.g., cyclopentanecarboxylic acid) with sulfur in the presence of a strong base such as lithium diethylamide.

The preparation of the compounds of the invention according to process (b) involving the condensation of an acid of formula IV with an amino acid ester of formula V is carried out in a similar fashion to process (a). Similarly, the starting materials of formula IV are prepared by condensation of an acid of formula III with an ester corresponding to gem-disubstituted amino acids of formula IX (wherein $R_8$ is now hydrogen) under conditions similar to those described above, followed by removal of the carboxyl protecting group.

The preparation of the compounds of the invention according to process (c) involving the displacement of a leaving group Y in a compound of formula VI with a thiol derivative $R_3'$—SH as a salt thereof is carried out according to methods well-known in the art.

A reactive esterified hydroxyl group, represented by Y, is a hydroxyl group esterified by a strong inorganic or organic acid. Corresponding Y groups are in particular halo, for example, chloro, bromo or iodo, also sulfonyloxy groups, such as lower alkyl- or arylsulfonyloxy groups, for example, (methane-, ethane-, benzene- or toluene-) sulfonyloxy groups, also the trifluoromethylsulfonyloxy group.

The displacement is carried out in an inert solvent, such as dimethylformamide or methylene chloride in the presence of a base such as potassium carbonate, triethylamine, diisopropylethylamine, N-methylmorpholine, and the like at room or elevated temperature. Using a salt of $R_3'SH$ (e.g., potassium thioacetate), the reaction is carried out in the absence of a base, in an inert solvent such as tetrahydrofuran or dimethylformamide.

Similarly, the starting materials of formula VI can be prepared by reacting the dipeptide derivative of formula II with an acid of the formula

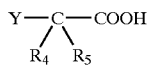
(X)

wherein $R_4$ and $R_5$ and Y have meaning as defined above, under conditions described for process (a).

The compounds of formula X wherein Y is halo, such as the α-bromocarboxylic acids are known and are prepared, e.g., as described in International Application WO 99/55726 published Nov. 4, 1999.

The compounds of the invention and intermediates, e.g., those of formulas II, V and VI, having the side chain alk-X-$R_1$ are prepared from the corresponding compounds having the alk-X' side chain wherein X' represents amino, hydroxy, thiol or a suitable leaving group according to methodology known in the art and illustrated herein. For example, the acids and esters of formula V can be obtained starting with serine, homoserine, threonine, cysteine and the like, preferably in optically active form.

Certain compounds of the invention and intermediates can be converted to each other according to general reactions well-known in the art.

The free mercaptans may be converted to the S-acyl derivatives by reaction with a reactive derivative of a carboxylic acid (corresponding to $R_3$ being acyl in formula I), such as an acid anhydride or said chloride, preferably in the presence of a base such as triethylamine in an inert solvent such as acetonitrile or methylene chloride.

Free alcohols and phenols can be converted to the corresponding acyl derivatives, e.g., by reaction with a corresponding acid chloride in the presence of a base, such as triethylamine.

The free mercaptans, wherein $R_3$ represents hydrogen, may be oxidized to the corresponding disulfides, e.g., by air oxidation or with the use of mild oxidizing agents such as iodine in alcoholic solution. Conversely, disulfides may be reduced to the corresponding mercaptans, e.g., with reducing agents such as sodium borohydride, zinc and acetic acid or tributylphosphine.

Carboxylic acid esters may be prepared from a carboxylic acid by condensation with, e.g., the halide corresponding to $R_2$—OH, in the presence of a base, or with an excess of the alcohol in the presence of an acid catalyst, according to methods well-known in the art.

Carboxylic acid esters and S-acyl derivatives may be hydrolyzed, e.g., with aqueous alkali such as alkali metal carbonates or hydroxides. S-acyl and ester groups can be selectively removed as illustrated herein.

Preferably, and wherever possible, the preferred isomers of the invention of formula Ia are prepared from pure enantiomers.

In case mixtures of stereoisomers (e.g., diastereomers) are obtained, these can be separated by known procedures such as fractional crystallization and chromatography (e.g., thin layer, column, flash chromatography). Racemic free acids can be resolved into the optical antipodes by fractional crystallization of d- or l-(α-methylbenzylamine, cinchonidine, cinchonine, quinine, quinidine, dehydroabiethylamine, brucine or strychnine) salts and the like. Racemic products, if not diastereoisomers, can first be converted to diastereoisomers with optically active reagents (such as optically active alcohols to form esters) which can then be separated as described above, and, e.g., hydrolyzed to the individual enantiomer. Racemic products can also be resolved by chiral chromatography, e.g., high pressure liquid chromatography using a chiral absorbent; also by enzymatic resolution, e.g., of esters with alkalase.

The above-mentioned reactions are carried out according to standard methods, in the presence or absence of diluents, preferably such as are inert to the reagents and are solvents thereof, of catalysts, alkaline or acidic condensing or said other agents respectively and/or inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, for inhibiting both ACE and NEP, and, e.g., for the prevention or treatment of cardiovascular disorders such as hypertension, edema, salt retention and congestive heart failure, either alone or in combination with one or more other agents which are useful for the treatment of such disorders. Such may be anti-hypertensive agents, anti-atherosclerotic agents, cardiac agents, diuretic agents, antidiabetic agents, cholesterol-lowering agents and the like. When used in combination with other therapeutic agents such can be administered separately or in a fixed combination.

Examples of therapeutic agents which can be used in combination are angiotensin II receptor antagonists, such as valsartan, losartan, candesartan, eprosartan, irbesartan and telmisartan; β-blockers, such as bisoprolol, propanolol, atenolol, sotalol and metoprolol; renin inhibitors; calcium channel blockers, such as amlodipine, verapamil, diltiazem, bepridil, felodipine, isradipine, nicardipine, nifedipine, nimodipine and nisoldipine; aldosterone synthase inhibitors/aldosterone antagonists, such as eplerenone, (+)-fadrozole (WO 01/76574), spironolactone and canrenone; diuretics, such as furosemide, hydrochlorothiazide, indapamide, metazolone, amiloride and triamterene; vasopressin receptor antagonists, such as OPC 21268, SR 49059, SR121463A, SR49059, VPA985, OPC31260 and YM087; cardiotonic drugs, such as enoximone and levosimendan; endothelin antagonists and ECE inhibitors, such as bosentan, BMS193884, TBC3711 and compounds disclosed in WO 99/55726; anti-atherosclerotic agents, particularly cholesterol lowering agents, such as bile acid sequestrants (e.g., cholestyramine and colestipol); cholesterol absorption inhibitors, such as ezetimibe; fibrates, such as fenofibrate and gemfibrozil; statin HMG CoA reductase inhibitors, such as atorvastatin, fluvastatin, lovastatin, pravastatin, simvastatin and pitavastatin; and nicotinic acid derivatives; thyromimetic agents, such as those disclosed in U.S. Pat. No. 5,569,674 and WO 00/58279; also antidiabetic agents, such as repaglinide, nateglinide, metformin, rosiglitazone, pioglitazone, glyburide, glipizide, glimepiride, DPP728, LAF237, NH622 and DRF4158.

The present invention also relates to the use of the compounds of the invention for the preparation of pharmaceutical compositions, especially pharmaceutical compositions having ACE and NEP inhibiting activity, and, e.g., anti-hypertensive activity.

The pharmaceutical compositions according the invention are those suitable for enteral, such as oral or rectal, transdermal and parenteral administration to mammals, including man, for the treatment of cardiovascular disorders, such as hypertension, comprising an effective amount of a pharmacologically active compound of the invention or a pharmaceutically acceptable salt thereof, alone or in combination with one or more pharmaceutically acceptable carriers, as well as in combination with other therapeutic agents also useful for the treatment of cardiovascular disorders, as indicated above.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient, together with a) diluents, e.g., lactose, dextrose, sucrose, mannitol, sorbitol, cellulose and/or glycine; b) lubricants, e.g., silica, talcum, stearic acid, its magnesium or calcium salts and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired, d) disintegrants, e.g., starches, agar, alginic acid or its sodium salt, or effervescent mixtures; and, if desired, absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1–75%, preferably about 1–50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50–70 kg may contain between about 10 and 200 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations (expressed in degrees) are measured at room temperature at 589 nM (D line of sodium) or other wave lengths as specified in the examples. The structure of the compounds are confirmed by standard analytical methods such as mass spectrum, elemental analysis, NMR, IR spectroscopy and the like.

The prefixes R and S are used to indicate the absolute configuration at each asymmetric center.

EXAMPLE 1

(a) N-[2-[(S)-2-Acetylthio-3-methylbutanoylamino]-2-methylpropionyl]-O-benzyl-L-serine ethyl ester

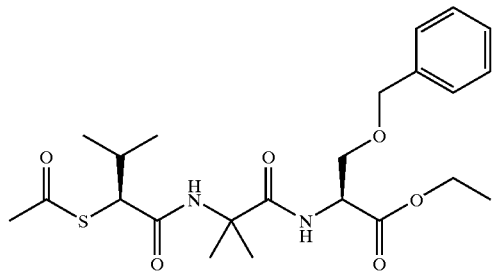

N-[2-[-[(R)-3-bromo-3-methylbutanoylamino]-2-methyl-proprionyl-O-benzyl-L-serine ethyl ester (4.96 g, 10.5 mmol) is dissolved in tetrahydrofuran (100 mL) and potassium thioacetate (6.00 g, 52.5 mmol) is added. The mixture is stirred at room temperature for 4 hours, then diluted with ethyl acetate (500 mL) and washed with water (100 mL), sodium bicarbonate solution (2×100 mL), water (2×100 mL) and then brine (50 mL). The solution is dried over sodium sulfate and concentrated in vacuo. The crude material is purified by flash chromatography (silica gel, 3:2 hexane/ethyl acetate) to yield title compound; m.p. 55–57° C.; $[\alpha]^{20}_D$ −63.5° (c=0.99, CH$_3$OH); MS(M+H):467.

Alternately, the above displacement can be carried out with 2 equivalents of potassium thioacetate in ethyl acetate at room temperature and the resulting product can be crystallized from t-butyl methyl ether/heptane (40/60) to give the title compound having m.p. of 68° C.

The starting material is prepared as follows:

A solution of O-benzyl-L-serine (9.75 g, 50 mmol) in ethanol (200 mL) is saturated with HCl gas for 8 minutes. The mixture is stirred overnight at room temperature, and then concentrated in vacuo. The solid is washed with diethyl ether and collected by filtration to yield O-benzyl-L-serine ethyl ester hydrochloride as a white solid.

To a solution of BOC-α-methylalanine (3.05 g, 15 mmol), O-benzyl-L-serine ethyl ester hydrochloride (3.89 g, 15 mmol), 1-ethyl-3-(3-dimethylaminopropyl)carbodiimide (EDCI, 2.88 g, 15 mmol) and 1-hydroxy-7-azabenzotriazole (HOAT, 2.04, 15 mmol) in methylene chloride (150 mL) is added triethylamine (1.52 g, 15 mmol). The mixture is stirred overnight and then concentrated in vacuo. The residue is re-dissolved in ethyl acetate and washed with water, 1 N HCl, water, and brine. The solution is dried over sodium sulfate and concentrated to yield N-[2-(BOC-amino)-2-methylpropionyl]-O-benzyl-L-serine ethyl ester of the formula

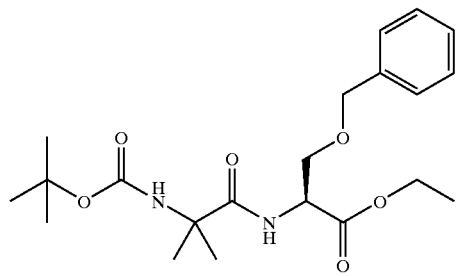

Alternately, the above carbamate can be prepared by condensing O-benzyl-L-serine ethyl ester hydrochloride with BOC-α-methylalanine in the presence of 1 equivalent of 2-chloro-4,6-dimethoxy-1,3,5-triazine (CDMT, see Synthesis, pp. 917–920 (1987)) and N-methylmorpholine (2.5 equivalents) in ethyl acetate at room temperature.

The above carbamate (6.12 g, 15 mmol) is dissolved in methylene chloride (200 mL) and chilled in an ice bath. The solution is saturated with HCl gas for 10 minutes and then stirred at room temperature overnight. The residue is concentrated. Methylene chloride is added and the residue is concentrated again to give N-(2-amino-2-methylpropionyl)-O-benzyl-L-serine ethyl ester hydrochloride as a foam; MS(M+H):309.

Alternately, N-(2-amino-2-methylpropionyl)-O-benzyl-L-serine hydrochloride can be prepared by treating the carbamate with HCl gas (3 equiv.) in ethyl acetate at a temperature of 25–50° C. for 3 hours.

To a solution of the above amine hydrochloride (4.90 g, 14 mmol) in methylene chloride (150 mL) is added (R)-2-bromo-3-methylbutanoic acid diisopropyl amine salt (4.03 g, 14 mmol), 1-ethyl-3-(3-dimethylaminopropyl)carbodiimide hydrochloride (EDCI, 2.70 g, 14 mmol) and 1-hydroxy-7-azabenzotriazole (HOAT, 1.90 g, 14 mmol). The mixture is stirred at room temperature overnight and then concentrated in vacuo. The residue is dissolved in ethyl acetate and washed with water, dilute sodium bicarbonate, water, 1 N HCl, and then brine. The solution is dried over sodium sulfate and concentrated to give a solid. The solid is purified by flash chromatography (silica gel, 2:1 hexane/ethyl acetate) to give N-[2-(R)-2-bromo-3-methylbutanoylamino]-2-methylpropionyl]-O-benzyl-L-serine ethyl ester of the formula

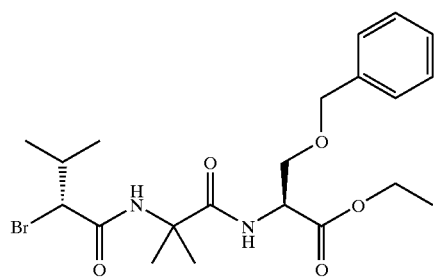

Alternately, the above condensation of (R)-2-bromo-3-methylbutanoic acid diisopropylamine salt with the amine hydrochloride can be carried out in acetonitrile in the presence of CDMT (1.05 equiv.) and N-methyl-morpholine (1.5 equiv.) at a temperature of 5–25° C.

Similarly prepared are:

(b) N-[2-[(S)-2-acetylthio-3,3-dimethylbutanoylamino]-2-methylpropionyl]-O-benzyl-L-serine ethyl ester

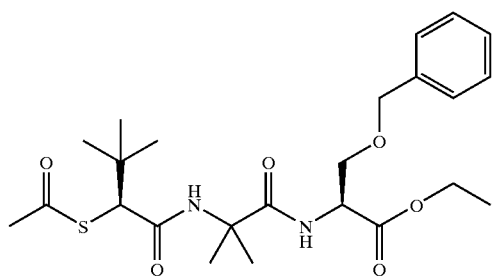

(c) N-[2-[(S)-2-acetylthio-3-methylbutanoylamino]-2-methylpropionyl]-O-benzyl-L-threonine ethyl ester; m.p. 121–122° C.

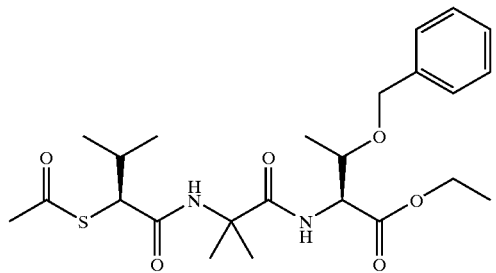

(d) N-[2-[(S)-2-acetylthio-3-methoxybutanoylamino]-2-methylpropionyl]-O-benzyl-L-serine ethyl ester; $[\alpha]_D^{20}$+14.9° (c=1.04, DMSO)

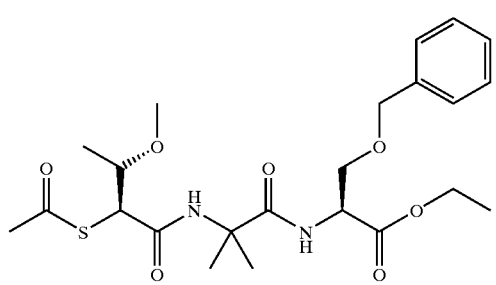

(e) N-[2-[(S)]-2-acetylthio-3-methylpentanoy-
lamino]-2-methylpropionyl]-O-benzyl-L-serine ethyl
ester; $[\alpha]_D^{20}$ −6.93° (c=1.09, CH$_3$OH)

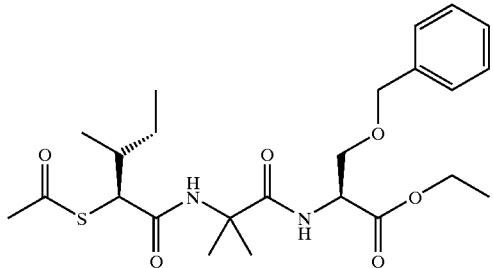

(f) N-[2-[(S)-2-acetylthio-3-methylbutanoylamino]-
2-methylpropionyl]-O-(3-trifluoromethylbenzyl)-L-
serine ethyl ester

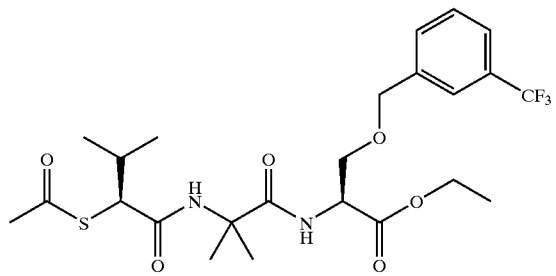

The starting O-(3-trifluoromethylbenzyl)-L-serine ethyl ester hydrochloride is prepared as follows:

To a suspension of sodium hydride (60% in oil, 3.04 g, 76 mmol) in N,N-dimethylformamide (60 mL) at 0° C. is added BOC-L-serine (7.80 g, 38 mmol). The mixture is stirred for 1 hour and then m-trifluoromethylbenzyl chloride (7.39 g, 38 mmol) is added. The mixture is allowed to warm to room temperature and is stirred overnight. The mixture is quenched with water. Ethyl acetate is added and the mixture is washed with brine, dried over MgSO$_4$ and concentrated to give a yellow oil which is purified by flash chromatography (SiO$_2$; hexane/ethyl acetate) to give a clear oil. The residue is dissolved in ethanol (120 mL), the solution is cooled to 0° C. and saturated with HCl gas for 5 minutes. The mixture is allowed to warm to room temperature and stirred overnight. The mixture is concentrated to give O-(4-trifluoromethyl-benzyl)-L-serine ethyl ester hydrochloride.

(g) N-[2-[(S)-2-acetylthio-3-methylbutanoylamino]-
2-methylpropionyl]-O-(4-fluorobenzyl)-L-serine
ethyl ester as an oil

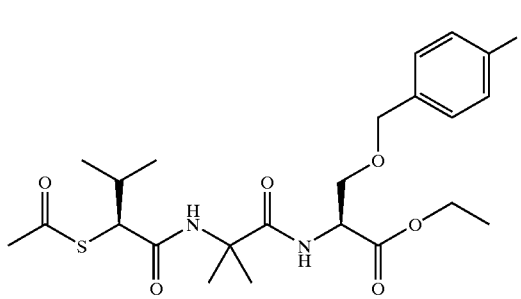

(h) N-[2-[(S)-2-acetylthio-3-methylbutanoylamino]-
2-methylpropionyl]-O-(4-fluorophenyl)-L-ho-
moserine ethyl ester as an oil

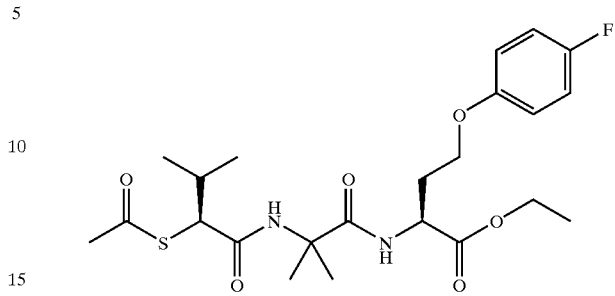

The starting O-(4-fluorophenyl)-L-homoserine ethyl ester hydrochloride is prepared as follows:

To a solution of BOC-L-homoserine t-butyl ester (3.2 g, 11.6 mmol) in tetrahydrofuran is added triphenylphosphine (7.59 g, 29 mmol), p-fluorophenol (2.08 g, 18.6 mmol) and 1,1'-azobis(N,N-dimethylformamide) (3.2 g, 18.6 mmol). The mixture is stirred overnight, washed with brine, dried over MgSO$_4$, and the solvent is removed to give an orange oil. The oil is purified by flash chromatography (SiO$_2$, 85% hexane/15% ethyl acetate) to give a clear oil which is dissolved in ethanol (100 mL) and the solution is saturated with HCl gas, then stirred overnight. The mixture is concentrated to give O-(4-fluorophenyl)-L-homoserine ethyl ester hydrochloride as a white solid.

(i) N-[2-[(S)-2-acetylthio-3-methyl-butanoylamino]-
2-methylpropionyl]-O-(3-fluorophenyl)-L-ho-
moserine ethyl ester

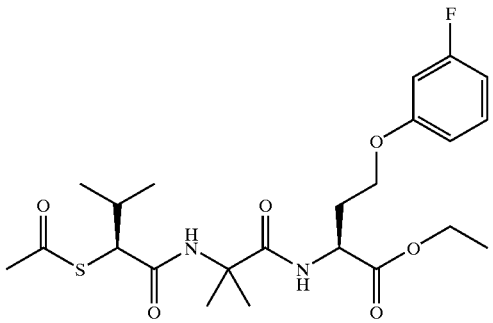

(j) N-[2-[(S)-2-acetylthio-3-methylbutanoylamino]-
2-methylpropionyl]-O-benzyl-L-serine morpholi-
nocarbonylmethyl ester, purified by chromatogra-
phy on silica gel with hexane, ethyl acetate,
methanol (20:70:10) as a white solid

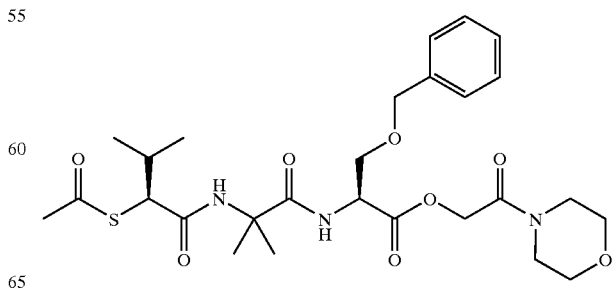

The starting material is prepared as follows:

O-Benzyl-L-serine (10.0 g, 51.3 mmol), di-tert-butyl-dicarbonate (11.2 g, 51.4 mmol) and 1 N sodium hydroxide (103 mL, 103 mmol) are stirred together in 100 mL of dioxane at room temperature for 16 hours. The mixture is concentrated in vacuo, taken up in water, acidified to pH 1 with 6 N HCl and extracted with ethyl acetate. The organic layer is washed with water, then brine, and dried over anhydrous magnesium sulfate. The mixture is filtered and concentrated in vacuo to give BOC-O-benzyl-L-serine as an oil. 4-(2-Chloroacetyl)morpholine (1.22 g, 7.48 mmol) is added to a solution of BOC-O-benzyl-L-serine (2.20 g, 7.46 mmol), triethylamine (0.75 g, 7.43 mmol) and sodium iodide (0.11 g, 0.73 mmol) in 5 mL of N,N-dimethylformamide and the mixture stirred at room temperature for 2 hours. The mixture is diluted with ethyl acetate, washed with water, then with brine, and dried over anhydrous magnesium sulfate. The mixture is filtered and concentrated in vacuo to give a yellow oil. The oil is chromatographed on silica gel with hexane:ethyl acetate:methanol (35:60:5) to give BOC-O-benzyl-L-serine morpholinocarbonylmethyl ester as a colorless oil. HCl gas is bubbled through a solution of the carbamate ester (1.72 g, 4.08 mmol) in methylene chloride (50 mL) for 5 minutes and the mixture is stirred at room temperature for 3 hours. The resulting mixture is concentrated in vacuo to yield O-benzyl-L-serine morpholinocarbonylmethyl ester as a foam.

(k) N-[2-[(S)-2-acetylthio-3-methylbutanoylamino]-2-methylpropionyl]-O-benzyl-L-serine dimethylaminocarbonylmethyl ester, prepared and purified as described for compound of Example 1(j)

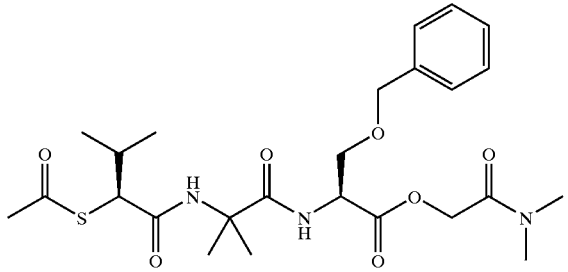

(l) N-[2-[(S)-2-acetylthio-3-methylbutanoylamino]-2-methylpropionyl]-O-benzyl-L-serine diethylaminocarbonylmethyl ester, prepared as described for compound of Example 1(j) and purified by chromatography on silica gel with hexane, ethyl acetate, methanol (35:60:5)

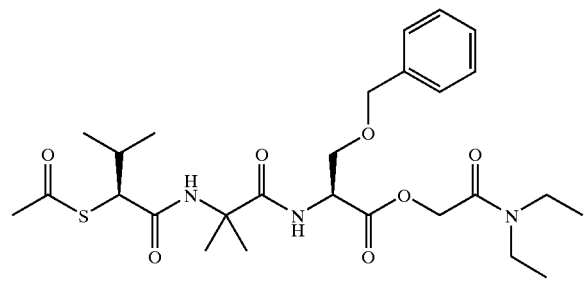

(m) N-[2-[(S)-2-[methoxyacetyl)thio]-3-methylbutanoylamino]-2-methylpropionyl]-O-benzyl-L-serine ethyl ester; $[\alpha]_D$–55.27°; (c=1.084, CH$_3$OH)

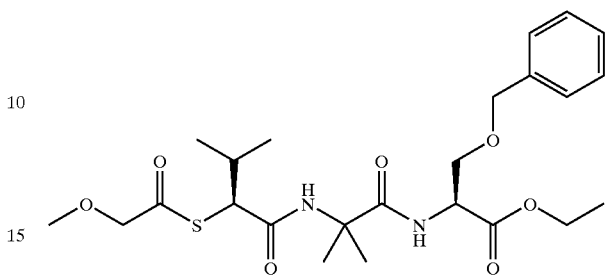

(n) N-[2-[(S)-2-[(morpholinoacetyl)thio]-3-methylbutanoylamino]-2-methylpropionyl]-O-benzyl-serine ethyl ester; $[\alpha]_D$–48.61° (c=1.098, CH$_3$OH)

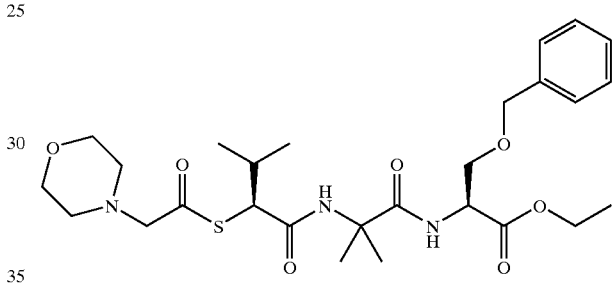

(o) N-[2-[(S)-2-acetylthio-2-(4-tetrahydropyranyl)acetylamino]-2-methylpropionyl]-O-benzyl-L-serine ethyl ester; $[\alpha]_D^{20}$–55.4° (c=0.83, DMSO)

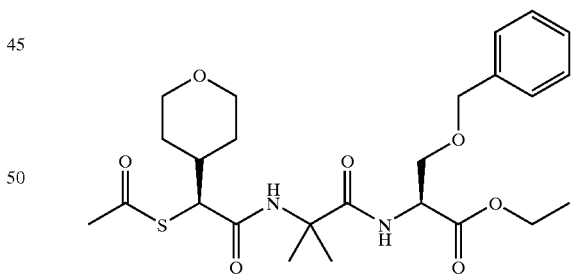

The starting (D)-α-bromo-α-(4-tetrahydropyranyl)-acetic acid can be prepared as follows:

A solution of sodium nitrite (4.71 g, 68.3 mmol) in 35 mL of water is added dropwise to a chilled (0° C.) solution of (D)-α-bromo-α-(4-tetrahydropyranyl)-glycine (J. Am. Chem. Soc., Vol. 117, pp. 9375–9376 (1995) (7.05 g, 44.3 mmol) and 48% HBr (aq) (70 mL) in 35 mL of water. Upon completion of the addition, the mixture is allowed to warm to room temperature and stirred at room temperature for 3 hours. The mixture is extracted with ethyl acetate; the organic layer is washed sequentially with water, 5% aqueous sodium thiosulfate, and brine, then dried over anhydrous magnesium sulfate. The mixture is filtered and concentrated in vacuo to yield (D)-α-bromo-α-(4-tetrahydropyranyl)-acetic acid as a solid.

(p) N-[2-[(S)-2-[(1-(1,2,4)-triazolyl)acetylthio]-3-methylbutanoylamino]-2-methylpropionyl]-O-benzyl-L-serine ethyl ester; m.p. 106–107°; [α]$_D$–61.46° (c=1.09, CH$_3$OH)

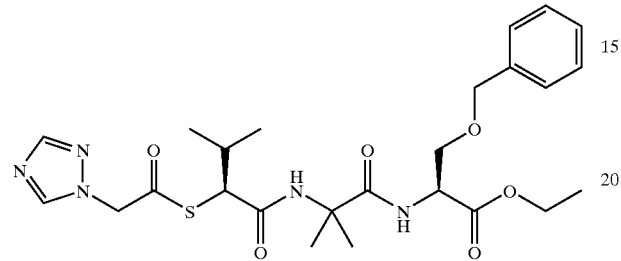

(q) N-[2-[(S)-2-[(4-methylpiperazino)acetylthio]-3-methylbutanoylamino]-2-methylpropionyl]-O-benzyl-L-serine ethyl ester; m.p. 95–96°; [α]$_D$–48.5° (c=0.935, CH$_3$OH)

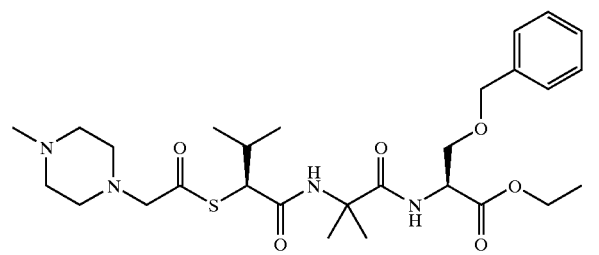

(r) N-[2-[(S)-2-acetylthio-3-methylbutanoylamino]-2-ethylbutanoyl]-O-benzyl-L-serine ethyl ester; [α]$_D$–83.6° (c=1.07, CH$_3$OH)

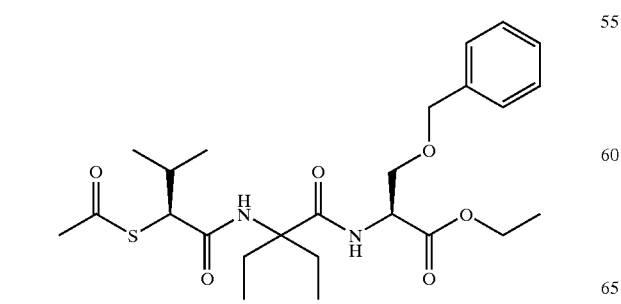

(s) N-[2-[(S)-2-(morpholinoacetylthio)-3,3-dimethylbutanoylamino]-2-methylpropionyl]-O-benzyl-L-serine ethyl ester; [α]$_D$–55.5° (c=1.008, DMSO)

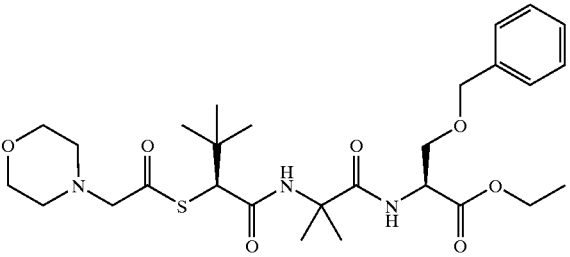

(t) N-[2-[(S)-2-[(methoxyacetyl)thio]-3,3-dimethylbutanoylamino]-2-methylpropionyl]-O-benzyl-L-serine ethyl ester; [α]$_D$–61.67° (c=1.024, DMSO)

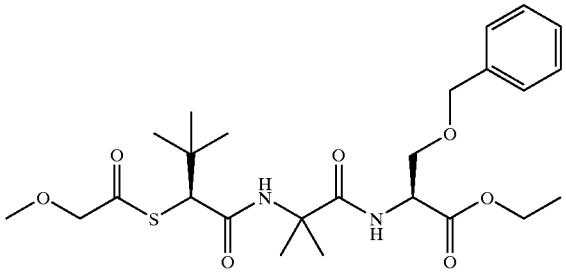

(u) N-[2-[(S)-2-(acetylthio)pentanoylamino]-2-methylpropionyl]-O-benzyl-L-serine ethyl ester

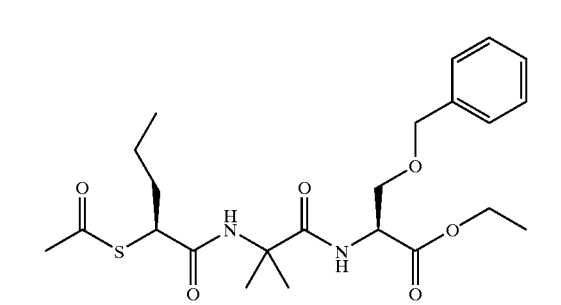

(v) N-[2-[(S)-2-acetylthio-3-methylbutanoylamino]-2-methylpropionyl]-O-(4-biphenylylmethyl)-L-serine ethyl ester

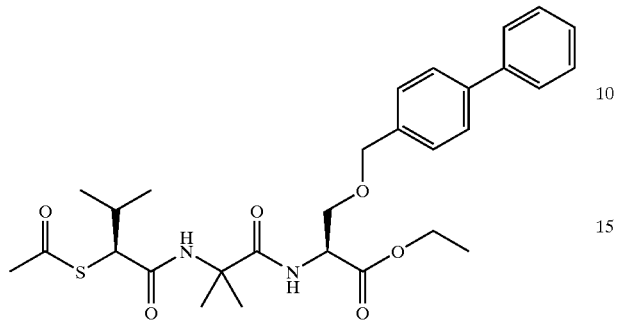

EXAMPLE 2

N-[2-[(S)-2-Acetylthio-3-methylbutanoylamino]-2-methylpropionyl]-S-benzyl-L-cysteine ethyl ester

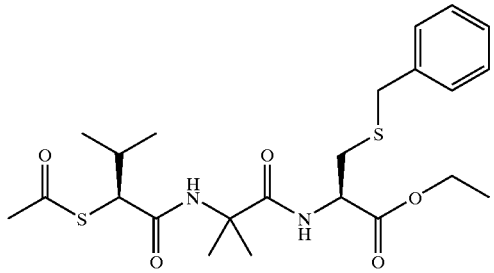

The title compound is prepared similarly to Example 1 and re-crystallized from methyl t-butyl ether/hexane, m.p. 69–71° C.

The starting material is prepared as follows:

HCl(g) is bubbled into a solution of BOC-S-benzyl-L-cysteine (9.33 g, 30 mmol) in ethanol (200 mL) for 15 minutes. The container is stoppered and stirred at room temperature overnight. The solvent is evaporated in vacuo and the residue stirred in diethyl ether (150 mL) for 1.5 hours to yield S-benzyl-L-cysteine ethyl ester hydrochloride as a solid.

A mixture of S-benzyl-L-cysteine ethyl ester hydrochloride (7.98 g, 29 mmol), BOC-α-methylalanine (5.89 g, 29 mmol), triethylamine (2.93 g, 29 mmol), 1-hydroxybenzotriazole (HOBT, 3.92 g, 29 mmol) and EDCI (5.57 g, 29 mmol) in methylene chloride (200 mL) is stirred under an argon atmosphere at room temperature overnight. The reaction mixture is evaporated to dryness and the residue is dissolved in ethyl acetate (200 mL). The solution is washed with water (50 mL), 1 N HCl (50 mL), water (50 mL), 5% sodium bicarbonate (50 mL), water (50 mL) and finally brine (25 mL). The solution is then dried over sodium sulfate, filtered and evaporated to dryness to give N-[2-(BOC-amino)-2-methylpropionyl]-S-benzyl-L-cysteine ethyl ester.

EXAMPLE 3

N-[2-[(S)-2-Acetylthio-3-methylbutanoylamino]-2-methylpropionyl]-(S)-2-amino-3-(benzylsulfonyl)-propionic acid ethyl ester

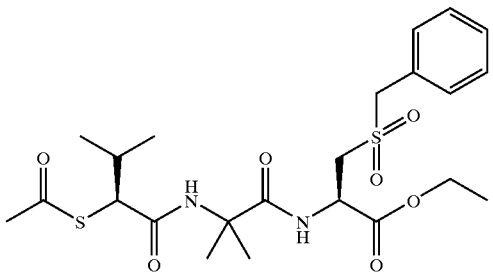

The above compound is prepared similarly to Example 1. The starting material is prepared as follows:

To a solution of N-[2-(BOC-amino)-2-methylpropionyl]-S-benzyl-L-cysteine ethyl ester (7.21 g, 17 mmol) in methylene chloride (250 mL) under an argon atmosphere is added m-chloro-perbenzoic acid (8.77 g, 51 mmol) and the mixture is stirred overnight at room temperature. The mixture is evaporated to dryness and the residue is dissolved in ethyl acetate (300 mL). The solution is washed with 5% sodium bicarbonate (3×50 mL), water (50 mL) and brine (25 mL). The solution is dried over sodium sulfate, filtered and evaporated in vacuo to give N-[2-(BOC-amino)-2-methylpropionyl]-(S-)2-amino-3-(benzylsulfonyl)-propionic acid ethyl ester.

EXAMPLE 4

(a) $N^2$-[2-[(S)-2-Acetylthio-3-methylbutanoylamino]-2-methylpropionyl]-(S)-2-amino-3-(benzoylamino)-propionic acid methyl ester

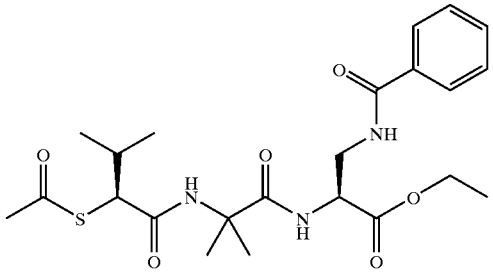

A mixture of benzoyl chloride (0.085 mL, 0.73 mmol), $N^2$-[2-[(S)-2-acetylthio-3-methylbutanoylamino]-2-methylpropionyl]-(S)-2,3-diaminopropionic acid methyl ester hydrochloride (0.29 g, 0.73 mmol) and triethylamine (0.15 mL, 1.49 mmol) in methylene chloride (10 mL) is stirred at room temperature for 16 hours. The reaction mixture is evaporated to dryness in vacuo, the residue is dissolved in ethyl acetate, and the solution is washed with water, then with saturated sodium bicarbonate solution and brine, dried over anhydrous magnesium sulfate, and evaporated to dryness to give an oil. The oil is chromatographed on silica gel with hexane, ethyl acetate (50:50) to yield the title compound as a white foam; m.p. 48–54° C.

(b) Similarly prepared is $N^2$-[2[(S)-2-acetylthio-3-methylbutanoylamino]-2-methylpropionyl]-(S)-2-amino-3-(benzenesulfonamido)propionic acid methyl ester; m.p. 47–51° C.; $[\alpha]_D^{20}$ –41.72 (c=1.03, $CH_3OH$)

The starting material is prepared as follows:

A mixture of (S)-2-amino-3-(BOC-amino)-propionic acid methyl ester hydrochloride (4.6 g, 2.1 mmol), N-CBZ-α-methylalanine (5.0 g, 2.1 mmol), HOAT (2.87 g, 2.1 mmol), EDCI (4.02 g, 2.1 mmol) and triethylamine (2.93 g, 2.1 mmol) in methylene chloride (50 mL) is stirred at room temperature for 16 hours. The reaction mixture is washed with brine, dried over anhydrous magnesium sulfate and concentrated in vacuo. The resulting oil is chromatographed on silica gel with hexane and ethylacetate (1:1) to yield $N^2$-[2-(CBZ-amino)-2-methylpropionyl]-(S)-2-amino-3-(BOC-amino)-propionic acid methyl ester as a white foam; m.p. 100–101° C.

A mixture of the above product (2.14 g, 4.90 mmol) and 10% palladium on charcoal (0.27 g) in ethanol (50 mL) is hydrogenated under 45 psi pressure in a Parr bottle for 4 hours. The mixture is filtered through a pad of Celite and concentrated in vacuo to give $N^2$-[2-amino-2-methylpropionyl]-(S)-2-amino-3-(BOC-amino)-propionic acid methyl ester hydrochloride as an oil.

A solution of the above product (2.28 g, 8.09 mmol), (R)-2-bromo-3-methylbutanoic acid diisopropyl amine salt (2.16 g, 7.13 mmol), EDCI (1.43 g, 7.49 mmol) and HOAT (1.15 g, 8.52 mmol) in methylene chloride (75 mL) is stirred at room temperature for 16 hours. The reaction mixture is evaporated to dryness in vacuo and the residue taken up in ethyl acetate. The ethyl acetate solution is washed with water, saturated sodium bicarbonate solution and brine, and then dried over anhydrous magnesium sulfate, and concentrated in vacuo. The resulting oil is chromatographed on silica gel with hexane and ethyl acetate (40:60) to give $N^2$-[2-[(R)-2-bromo-3-methylbutanoylamino]-2-methylpropionyl]-(S)-2-amino-3-(BOC-amino)-propionic acid methyl ester as a white foam.

A mixture of the above product (1.31 g, 2.82 mmol) and potassium thioacetate (1.28 g, 11.2 mmol) in tetrahydrofuran (50 mL) is stirred at room temperature for 4 hours and diluted with ethyl acetate. The mixture is washed with water, saturated sodium bicarbonate solution, brine and then dried over magnesium sulfate. The reaction mixture is concentrated to dryness in vacuo and the resulting oil is chromatographed on silica gel with hexane and ethyl acetate (40:60) to give N-[2-[(S)-2-acetylthio-3-methylbutanoylamino]-2-methylpropionyl]-(S)-2-amino-3-(BOC-amino)-propionic acid methyl ester.

Hydrogen chloride gas is bubbled through a solution of the above compound (1.01 g, 2.19 mmol) in 50 mL of methylene chloride for about 5 minutes, the mixture is stirred at room temperature for 3 hours, and then concentrated in vacuo to yield $N^2$-[2-[(S)-2-acetylthio-3-methylbutanoylamino]-2-methylpropionyl]-(S)-2,3-diaminopropionic acid methyl ester hydrochloride.

EXAMPLE 5

To a solution of 1-[(R)-2-bromo-3-methylbutanoylamino]cyclopentanecarboxylic acid (1 g, 3.42 mmol), O-benzyl-L-serine ethyl ester hydrochloride (0.89 g, 3.42 mmol), dicyclohexylcarbodiimide (0.7 g, 3.42 mmol) and 1-hydroxy-7-azabenzotriazole (0.47 g, 3.42 mmol) in methylene chloride is added triethylamine (0.48 mL, 3.42 mmol). The mixture is stirred for 24 hours and then washed with brine and concentrated in vacuo to give a light yellow oil. The residue is purified by flash chromatography (silica gel hexane/ethyl acetate) to give N-[1-(R)-2-bromo-3-methylbutanoylamino]-cyclopentanecarbonyl]-O-benzyl-L-serine ethyl ester of the formula

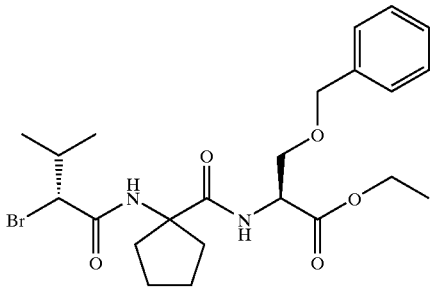

The bromo compound (0.7 g, 1.41 mmol) is dissolved in tetrahydrofuran (50 mL) and potassium thioacetate (0.19 g, 1.69 mmol) is added. The mixture is stirred at room temperature for 18 hours and then diluted with ethyl acetate and washed with brine, dried over magnesium sulfate and concentrated in vacuo to give yellow oil. The crude material is purified by flash chromatography (silica gel, hexane/ethyl acetate) to give a semi-solid which is triturated with hexane to yield N-[1-[(S)-2-acetylthio-3-methylbutanoylamino]-cyclopentanecarbonyl]-O-benzyl-L-serine ethyl ester of the formula

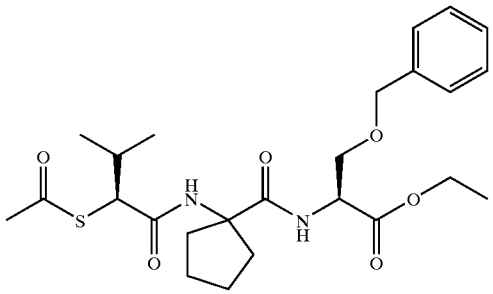

The 1-[(R)-2-bromo-3-methylbutanoylamino]cyclopentanecarboxylic acid starting material is prepared essentially by methodology described in WO 99/55726 by condensation of (R)-2-bromo-3-methylbutanoic acid diisopropylamine salt (prepared from L-valine) with cycloleucine methyl ester hydrochloride.

EXAMPLE 6

(a) N-[2-[(S)-2-Mercapto-3-methylbutanoylamino]-2-methylpropionyl]-O-benzyl-L-serine

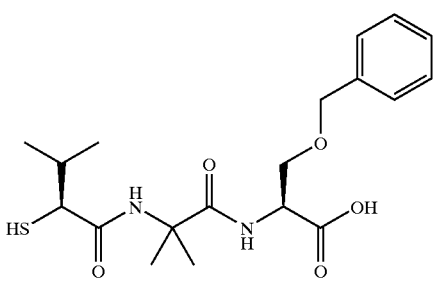

To a solution of the S-acetyl ethyl ester of Example 1 (0.47 g, 1 mmol) in methanol (10 mL) is added 1 N sodium hydroxide (5.0 mL, 5 mmol). The mixture is stirred at room temperature for 4 hours, acidified to pH 1 with 1 N HCl and then concentrated in vacuo. To the residue is added ethyl acetate. The mixture is washed with 1 N NaOH. The combined aqueous phase is then acidified and extracted with ethyl acetate. The organic phase is washed with brine, dried over sodium sulfate and then concentrated in vacuo. Trituration with hexane yields a white foam; m.p. 57–70° C.; $[\alpha]_D^{20}$–16.8° (c=1.032, DMSO); MS(M+H):397.

Similarly prepared are the following:

(b) N-[1-[(S)-2-mercapto-3-methylbutanoylamino]-cyclopentanecarbonyl]-O-benzyl-L-serine; m.p. 132–136° C. (crystallized from hexane/t-butylmethyl ether)

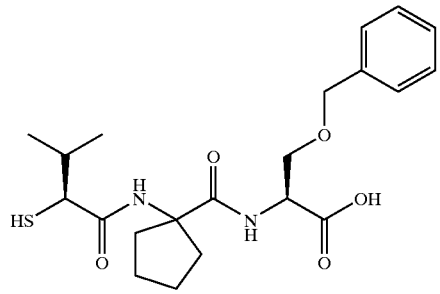

(c) N-[2-[(S)-2-mercapto-3-methylbutanoylamino]-2-methylpropionyl]-S-benzyl-L-cysteine; m.p. 81–87° C.; $[\alpha]_D^{20}$–37.87 (c=0.545, DMSO)

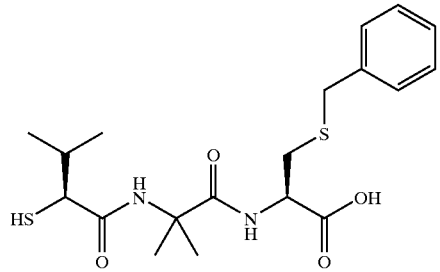

(d) N-[2-[(S)-2-mercapto-3-methylbutanoylamino]-2-methylpropionyl]-O-benzyl-L-threonine; m.p. 61–64° C.

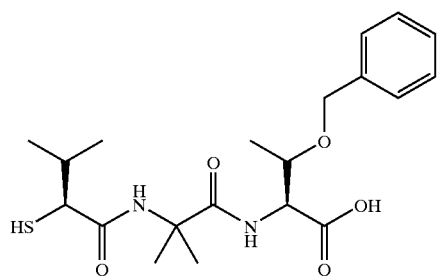

(e) N-[2-[(S)-2-mercapto-3,3-dimethylbutanoylamino]-2-methylpropionyl]-O-benzyl-L-serine; m.p. 128–130° C.; $[\alpha]_D$–2.46 (c=1.06, DMSO)

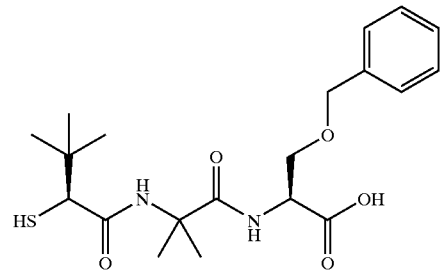

(f) N-[2-[(S)-2-mercapto-3-methylbutanoylamino]-2-methylpropionyl]-O-(4-fluorobenzyl)-L-serine; m.p. 50–54° C.

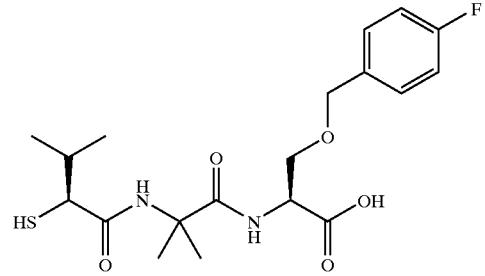

(g) N-[2-[(S)-2-mercapto-3-methylbutanoylamino]-2-methylpropionyl]-O-(4-fluorophenyl)-L-homoserine; m.p. 127–128° C.

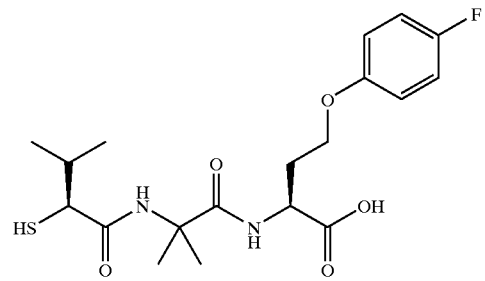

(h) N-[2-[(S)-2-mercapto-3-methylbutanoylamino]-2-methylpropionyl]-O-(3-fluorophenyl)-L-homoserine; m.p. 50–56° C.

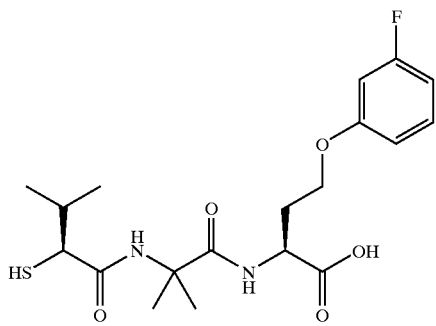

(i) N-[2-[(S)-2-mercapto-3-methoxybutanoylamino]-2-methylpropionyl]-O-benzyl-L-serine; $[\alpha]_D^{20}$+18.85 (c=0.997, DMSO)

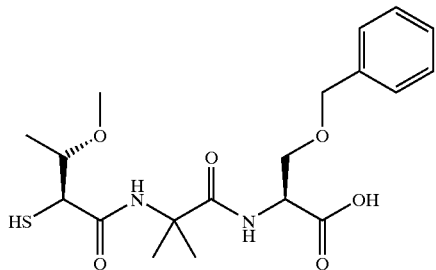

(j) N-[2-[(S)-2-mercapto-2-(4-tetrahydropyranyl)acetylamino]-2-methylpropionyl]-O-benzyl-L-serine; m.p. 184–189° C.; $[\alpha]_D^{20}$–24.94 (c=1.013, DMSO)

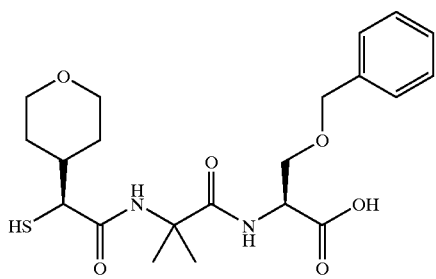

EXAMPLE 7

(a) N-[2-[(S)-2-mercapto-3-methylbutanoylamino]-2-methylpropionyl]-S-benzyl-L-cysteine ethyl ester

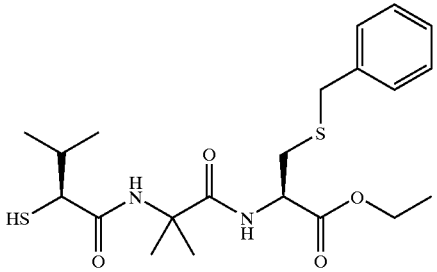

Under an argon atmosphere, the thioacetyl compound of Example 2 (0.48 g, 1.0 mmol) is dissolved in absolute EtOH (5 mL) and treated with 1 N NaOH of (1.0 mL, 1.0 mmol). The mixture is stirred for 4 hours at room temperature before treatment with 1 N HCl until pH 3. The mixture is evaporated to remove most of the EtOH and the aqueous residue is extracted with EtOAc (2×10 mL). The combined extracts are washed with H$_2$O (5 mL) and then with brine solution (5 mL). The solution is dried over Na$_2$SO$_4$, filtered and concentrated in vacuo. The product solidifies from tert-butyl methyl ether/hexane to give product; m.p. 87–91° C.

(b) Similarly prepared is N-[2-[(S)-2-mercapto-2-(4-tetrahydropyranyl)acetylamino]-2-methylpropionyl]-O-benzyl-L-serine ethyl ester; m.p. 85–93° C.; $[\alpha]_D$–37.21° (c=1.012, DMSO)

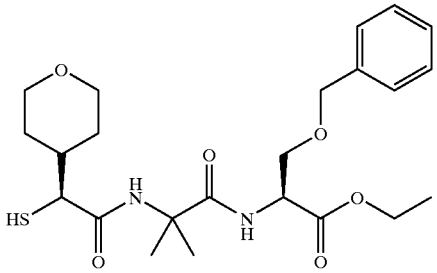

(c) Similarly prepared is N-[2-[(S)-2-mercapto-3,3-dimethylbutanoylamino]-2-methylpropionyl]-O-benzyl-L-serine ethyl ester; oil; $[\alpha]_D$–20.9° (c=1.025, DMSO)

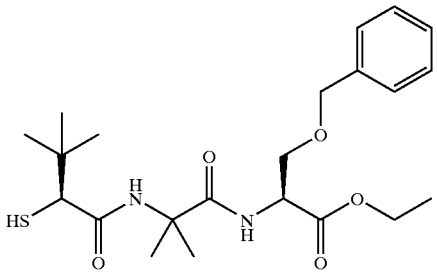

(d) similarly prepared is N-[2-[(S)-2-mercapto-3-methylbutanoylamino]-2-ethylbutanoyl]-O-benzyl-L-serine ethyl ester; [α]$_D$-31.48° (c=0.955, CH$_3$OH)

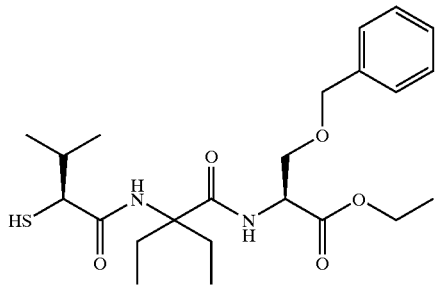

What is claimed is:
1. A compound of formula

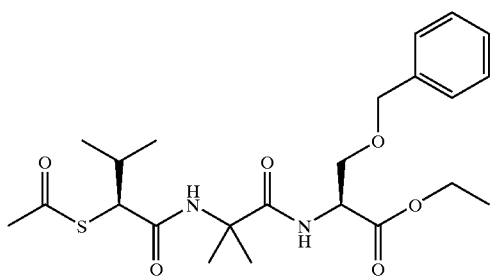

or pharmaceutically acceptable salts thereof.

2. The compound of claim 1 which is N-[2-[(S)-2-Acetylthio-3-methylbutanoylamino]-2-methylpropionyl]-O-ben-zyl-L-serine Ethyl.

3. A method of treating conditions which are responsive to ACE and NEP inhibition in mammals comprising administering to a mammal in need thereof an effective amount of a compound of claim 1.

4. The method of claim 3 wherein the conditions which are responsive to ACE and NEP inhibition are selected from the group consisting of hypertension, isolated systolic hypertension, renal failure, pulmonary edema, left ventricular hypertrophy, heart failure, atherosclerosis, elevated cholesterol plasma levels, pain, depression, certain psychotic conditions, cognitive disorders, angina, premenstrual syndrome, Meniere's disease, hyperaldosteronism, hypercalciuria, ascites, glaucoma, asthma, gastrointestinal disorders.

5. A method of treating conditions which are responsive to ECE inhibition in mammals comprising administering to a mammal in need thereof an effective amount of a compound of claim 1.

6. The method of claim 5 wherein the conditions which are responsive to ECE inhibition are selected from the group consisting of cerebral ischemia, subarachnoid hemorrhage, traumatic brain injury, cerebral vasospasm, arterial hypertrophy, restenosis, Raynaud's disease, myocardial infarction, obesity, prostate hyperplasia, migraine, diabetes mellitus, preeclampsia, glaucoma, transplantation rejection and erectile dysfunction.

7. A pharmaceutical composition comprising an effective amount of a compound of claim 1 in combination with one or more pharmaceutically acceptable carriers.

\* \* \* \* \*